(12) United States Patent
Kwun

(10) Patent No.: US 6,294,912 B1
(45) Date of Patent: Sep. 25, 2001

(54) METHOD AND APPARATUS FOR NONDESTRUCTIVE INSPECTION OF PLATE TYPE FERROMAGNETIC STRUCTURES USING MAGNETOSTRICTIVE TECHNIQUES

(75) Inventor: Hegeon Kwun, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/519,530

(22) Filed: Feb. 25, 2000

Related U.S. Application Data

(60) Provisional application No. 60/124,763, filed on Mar. 17, 1999.

(51) Int. Cl.[7] ............ G01N 27/82; G01N 29/04; G01N 9/24; G01R 33/12
(52) U.S. Cl. ............................................. 324/240; 73/643
(58) Field of Search ............................. 73/624, 629, 643, 73/598; 324/238, 239, 240, 209

(56) References Cited

U.S. PATENT DOCUMENTS

| | | |
|---|---|---|
| 3,555,887 | 1/1971 | Wood . |
| 4,127,035 * | 11/1978 | Vasile ................................ 73/643 |
| 4,881,031 | 11/1989 | Pfisterer et al. . |
| 5,456,113 | 10/1995 | Kwun et al. . |
| 5,457,994 | 10/1995 | Kwun et al. . |
| 5,544,207 | 8/1996 | Ara et al. . |
| 5,581,037 | 12/1996 | Kwun et al. . |
| 5,687,204 | 11/1997 | Ara et al. . |

* cited by examiner

*Primary Examiner*—Walter E. Snow
(74) *Attorney, Agent, or Firm*—Gunn, Lee & Keeling

(57) ABSTRACT

A method and apparatus is shown for implementing magnetostrictive sensor techniques for the nondestructive evaluation of plate type structures such as walls, vessels, enclosures, and the like. The system includes magnetostrictive sensors specifically designed for application in conjunction with plate type structures or pipes that generate guided waves in the plates or pipes which travel threrethrough in a direction parallel to the surface of the plate or pipe. Similarly structured sensors are positioned to detect the guided waves (both incident and reflected) and generate signals representative of the characteristics of the guided waves detected that are reflected from anomalies in the structure such as corrosion pits and cracks. The sensor structure is longitudinal in nature and generates a guided wave having a wavefront parallel to the longitudinal axis of the sensor, and which propagates in a direction perpendicular to the longitudinal axis of the sensor. The generated guided waves propagate in the plate within the path of the propagating wave. The reflected waves from these abnormalities are detected using a magnetostrictive sensor. Shear horizontal waves may also be created by rotating the magnetic bias 90° and used for similar inspection techniques. Pipes, which act as curved plates, may also be inspected as well as electric resistance welds therein.

17 Claims, 10 Drawing Sheets

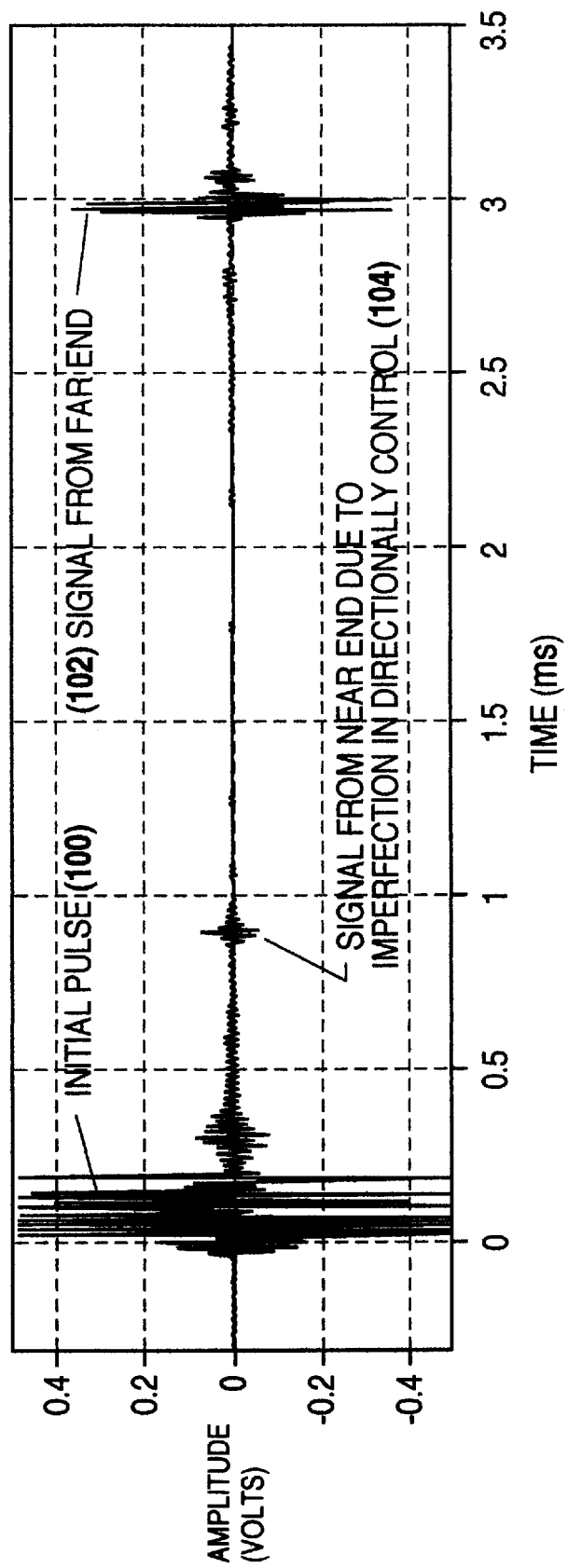

METHOD AND APPARATUS FOR NONDESTRUCTIVE INSPECTION OF PLATE TYPE FERROMAGNETIC STRUCTURES USING MAGNETOSTRICTIVE TECHNIQUES

This is a utility patent application where priority is claimed based on provisional Patent Application Serial No. 60/124,763, filed on Mar. 17, 1999.

BACKGROUND OF THE INVENTION

1. Field of the Invention

The present invention relates generally to methods and devices for the nondestructive evaluation of materials. The present invention relates more specifically to a magnetostrictive sensor based system for the long range inspection of plate type structures made from ferromagnetic materials.

2. Description of the Related Art

Magnetostrictive effect refers to the phenomena of a physical dimension change in ferromagnetic materials that occurs through variations in magnetization. In magnetostrictive applications, the generation and detection of mechanical waves is typically achieved by introducing a pulse current into a transmitting coil adjacent to a ferromagnetic material. The change in magnetization within the material located near the transmitting coil causes the material to change its length locally in a direction parallel to the applied field. This abrupt local dimension change, which is the magnetostrictive effect, generates a mechanical wave that travels at the speed of sound within the ferromagnetic material. When the mechanical wave is reflected back from the end of the ferromagnetic material, or from a defect in the ferromagnetic material, and reaches a detection coil, the mechanical wave generates a changing magnetic flux in the detection coil as a result of the inversed magnetostrictive effect. This changing magnetic flux induces an electric voltage within the detection coil that is proportional to the magnitude of the mechanical wave. The transmitting coil and the detection coil can be identical.

Advantages of using the magnetostrictive effect in nondestructive evaluation (NDE) applications include (a) the sensitivity of the magnetostrictive sensors, (b) durability of the magnetostrictive sensors, (c) no need to couple the sensor to the material being investigated, (d) long range of the mechanical waves in the material under investigation, (e) ease of implementation, and (f) low cost of implementation.

The use of magnetostrictive sensors (MsS) in the nondestructive evaluation (NDE) of materials has proven to be very effective in characterizing defects, inclusions, and corrosion within various types of ferromagnetic and non-ferromagnetic structures. A MsS launches a short duration (or a pulse) of elastic guided waves in the structure under investigation and detects guided wave signals reflected from anomalies such as defects in the structure. Since guided waves can propagate long distances (typically 100 feet or more), the MsS technique can inspect a global area of a structure very quickly. In comparison, other conventional NDE techniques such as ultrasonics and eddy current inspect only the local area immediately adjacent to the probes used. Therefore, the use of magnetostrictive sensors offers a very cost effective means for inspecting large areas of steel structures such as strands, cables, pipes, and tubes quickly with minimum support requirements such as surface preparation, scaffolding, and insulation removal. The ability to use magnetostrictive sensors with preparation of the object under inspection derives from the fact that direct physical contact between the sensors and the material is not required.

Efforts have been made in the past to utilize magnetostrictive sensor technologies in association with the inspection of both ferromagnetic and non-ferromagnetic materials. Included in these efforts are systems described in U.S. Pat. Nos. 5,456,113; 5,457,994; and 5,501,037, which are each commonly owned by the assignee of the present invention. The disclosures of U.S. Pat. Nos. 5,456,113; 5,457,994; and 5,501,037, provide background on the magnetostrictive effect and its use in NDE and are therefor incorporated herein by reference. These efforts in the past have focused primarily on the inspection of pipe, tubing and steel strands/cables wherein the geometry of the structure is such that the cross-sectional diameter is small in comparison to the length of the structure. While these systems and their application to longitudinal structures find significant applications, there are yet other structures that could benefit from the use of magnetostrictive based NDE.

Other efforts have been made in the past to utilize sensors that measure magnetic flux and/or acoustic waves in structural materials. These efforts have included those described in the following patents:

U.S. Pat. No. 3,555,887 issued to Wood on Jan. 19, 1971 entitled Apparatus for Electroacoustically Inspecting Tubular Members for Anomalies Using the Magnetostrictive Effect and for Measuring Wall Thickness. This patent describes a system designed to direct a mechanical wave through the thickness dimension of a long tubular member. The sensitivity of the device is limited to the directing of a wavefront normal to the surface of the material under inspection and immediately back to a sensor when reflected from an opposite wall or an anomaly.

U.S. Pat. No. 4,881,031 issued to Pfisterer, et al. on Nov. 14, 1989 entitled Eddy Current Method and Apparatus for Determining Structure Defects in a Metal Object Without Removing Surface Films or Coatings. This patent describes a method for establishing localized eddy currents within ferromagnetic materials and recognizes the presence and effect of a coating in order to identify and quantify corrosion beneath the coating. As with other eddy current methods, the ability to inspect a material is limited to the area immediately adjacent to the sensor.

U.S. Pat. No. 5,544,207 issued to Ara, et al. on Aug. 6, 1996 entitled Apparatus for Measuring the Thickness of the Overlay Clad in a Pressure Vessel of a Nuclear Reactor. This patent describes a system directed solely to the measurement of magnetic field variations that result from the distribution of the magnetic field through overlays of varying thickness. The system utilizes a magnetic yoke that is placed in close contact with the surface of the overlay clad of the pressure vessel.

U.S. Pat. No. 5,687,204 issued to Ara, et al. on Nov. 11, 1997 entitled Method of and Apparatus for Checking the Degradation of a Pressure Vessel of a Nuclear Reactor. This patent describes a system similar to the earlier issued Ara, et al. patent and utilizes a magnetic yoke having an excitation coil and a magnetic flux measuring coil that are placed in close contact with the inner wall of the pressure vessel. The hysteresis magnetization characteristics formed by the magnetic yoke and the pressure vessel wall are measured. Degradation of the material comprising the pressure vessel is inferred from a determination of the hardness of the material which is determined from the coercive forces obtained by analyzing the hysteresis characteristics of the magnetization.

BACKGROUND OF THE MAGNETOSTRICTIVE EFFECT

The nondestructive evaluation of materials using magnetostrictive sensors is based upon the magnetostrictive effect and its inverse effect. The magnetostrictive effect is a phenomenon that causes the physical dimensions of a ferromagnetic material to change slightly when the material is magnetized or demagnetized or otherwise experiences a changing magnetic field. The inverse effect is a phenomenon that causes a magnetic flux in the material to change when the material is stressed. Systems utilizing magnetostrictive sensors use the magnetostrictive effect and its inverse effect to generate and detect guided waves that travel through the ferromagnetic material.

In general, a magnetostrictive sensor consists of a conductive coil and a means for providing a DC bias magnetic field in the structure under inspection. The means for providing a bias magnetic field can include the use of either permanent magnets or electromagnets. In a transmitting magnetostrictive sensor, an AC electric current pulse is applied to the coil. The resulting AC magnetic field (a changing magnetic field) produces elastic waves (also known as guided waves) in an adjacent ferromagnetic material through the magnetostrictive effect. For pipes, cables, tubes, and the like, the waves are launched along the length of the longitudinal structure. In the receiving magnetostrictive sensor, a responsive electric voltage signal is produced in the conductive coil when the elastic waves (transmitted or reflected from anomalies within the material) pass the sensor location, through the inverse magnetostrictive effect.

With MsS techniques, defects are typically detected by using the pulse-echo method well known in the field of ultrasonics. Since the sensor relies on the magnetostrictive behavior found in ferrogmagnetic materials, this technology is primarily applicable to the inspection of ferromagnetic components such as carbon steel piping or steel strands. It is also applicable, however, to the inspection of nonferrous components if a thin layer of ferromagnetic material, such as nickel, is plated or coupled onto the component in the area adjacent to the magnetostrictive sensors.

The magnetostrictive sensor technique has the advantage of being able to inspect a large area of material from a single sensor location. Such sensors have, for example, been used to accurately inspect a length of pipe or cable of significantly more than 100 feet. Further, magnetostrictive sensor techniques are comprehensive in their inspection in that the methods can detect both internal and external defects, thereby providing a 100% volumetric inspection. The techniques are also quite sensitive, being capable of detecting a defect with a cross-section less than 1% of the total metallic cross-section of cylindrical structures such as pipes, tubes, or rods. Finally, as indicated above, magnetostrictive sensor techniques do not require direct physical contact between the component surface and the sensor itself. This eliminates the need for surface preparation or the use of a couplant.

APPLICATION TO PLATE TYPE AND CONTAINMENT STRUCTURES

In recent years, there have been many reported occurrences of steel liner containment vessels degrading at commercial nuclear power plants. Due to the aging of such facilities and the increased requirements for inspection, incidents of degradation are likely to increase. The structural degradation of these liners, especially corrosion damage, is an important concern since the liners are designed to provide a leak-tight pressure boundary for the nuclear material.

Many other industrial uses of plate type ferromagnetic materials could benefit from more frequent inspections to determine the state of deterioration, the location of faults, and the likelihood of failure. In most instances in the past, inspections of large plate type objects have required either very expensive off-line inspections or statistical samplings of randomly selected local areas that are for the most part less than reliable. It has heretofore been difficult to carry out a thorough inspection of a plate type structure, or a structure comprised of a plurality of plate type sheets of material, without high cost and long down time for the object under inspection. It would be desirable to use the magnetostrictive sensor technique for detecting and locating various anomaly characteristics within plate type materials. Such techniques could be used for detecting and locating wall thickness reductions in liners, such as those described above, that might be caused by corrosion over time. If such a system were applicable, it would be possible to inspect otherwise inaccessible regions of containment liners and the like that are either imbedded in concrete or adjacent to flooring or equipment that cannot be moved.

It would therefore be desirable to implement magnetostrictive sensor techniques in conjunction with plate type structures in a manner similar to, and with the accuracy of, such systems utilized in conjunction cylindrical structures. It would be desirable if an inspection of plate type structures could be carried out in an efficient manner that did not require full access to the surface of the plate. Such a magnetostrictive sensor system would be able to investigate large volumes of a plate type structure and would provide a cost effective global inspection of the structure.

SUMMARY OF THE PRESENT INVENTION

It is therefore an object of the present invention to provide a sensor device for implementing magnetostrictive based NDE in association with plate type structures in order to evaluate the condition of the structures and determine the presence of anomalies indicative of fractures, deteriorations, and the like.

It is a further object of the present invention to provide a magnetostrictive sensor appropriate for use in conjunction with the inspection of plate type structures that is capable of transmitting and receiving guided waves within the plate type structures and generating signals representative of the characteristics of such waves appropriate for the analysis and detection of anomalies therein.

It is a further object of the present invention to provide magnetostrictive sensor devices appropriate for use in conjunction with the inspection of plate type structures that inspect the entire structures for anomalies, corrosion, fractures, and the like in a cost effective manner.

It is a further object of the present invention to provide a method for the inspection of plate type structures that includes the use of a magnetostrictive sensor specifically adapted for directing guided waves into the plate type structures and detecting such waves as may be reflected from anomalies within the structure.

It is a further object of the present invention to provide a method and apparatus for the nondestructive evaluation of plate type structures utilizing magnetostrictive sensors that are capable of investigating large volumes of the plate type structures without access to the entire surface area of the plates.

It is yet another object of the present invention to provide a method and apparatus for nondestructive evaluation of plate type structures or containments having ferromagnetic materials through the use of a magnetostrictive sensor that may operate either in the symmetrical or anti-symmetrical Lamb wave mode.

It is yet another object of the present invention to provide a method and apparatus for nondestructive evaluation of plate type structures utilizing magnetostrictive sensors that generate and detect shear horizontal waves in the item being inspected.

It is yet another object of the present invention to provide a magnetostrictive sensor that is suitable for low frequency operation (200 kHz or less), has good sensitivity and long inspection range, and is relatively tolerate to liftoff.

It is yet another object of the present invention to provide a method and apparatus for inspecting electric resistance welding utilizing magnetostrictive sensors.

It is still another object of the present invention to provide a method and apparatus for nondestructive evaluation of pipes using magnetostrictive sensors that propagate guided waves in a circumferential direction around the pipe.

In fulfillment of these and other objectives, the present invention provides a method and apparatus for implementing magnetostrictive sensor techniques for the nondestructive evaluation of plate type structures such as walls, vessels, enclosures, and the like. The system includes magnetostrictive sensors specifically designed for application in conjunction with plate type structures that generate guided waves in the plates which travel through the plate in a direction parallel to the surface of the plate. Similarly structured sensors are positioned to detect the guided waves (both incident and reflected) and generate signals representative of the characteristics of the guided waves detected. The system anticipates the use of either discrete magnetostrictive transmitters and receivers or the use of a single magnetostrictive sensor that operates to both transmit and detect the guided waves. The sensor structure is longitudinal in nature and generates a guided wave having a wavefront parallel to the longitudinal direction of the sensor. Appropriate electronics associated with the process of generating the guided waves and controlling the propagation direction of the generated wave through the magnetostrictive transmitter as well as detecting, filtering, and amplifying the guided waves at the magnetostrictive receiver, are implemented as is well known in the art. Signal analysis techniques, also known in the art, are utilized to identify anomalies within the plate type structure. The method utilizes pattern recognition techniques as well as comparisons between signal signatures gathered over time from the installation of the structure under investigation to a later point after deterioration and degradation may have occurred.

By rotation of the magnetic field by 90°, the magnetostrictive sensor can be changed from operating in the symmetrical or the anti-symmetrical Lamb wave mode to a horizontal shear wave that is applied to the ferromagnetic material being inspected. In the horizontal shear wave mode, the DC bias magnetic field is in a direction perpendicular to the direction of wave propagation.

The magnetostrictive sensors can also be used to detect defects in electric resistance welding, such as pipes that are welded along a seam thereof. For example, a magnetostrictive transmitter can be placed on one side of the pipe being investigated and a magnetostrictive receiver on the other side of the pipe. By generation of a guided wave around the pipe, any defects in the pipe can immediately be detected, such as in the area of the weld.

DETAILED DESCRIPTION OF THE PREFERRED EMBODIMENT

Figure 1:
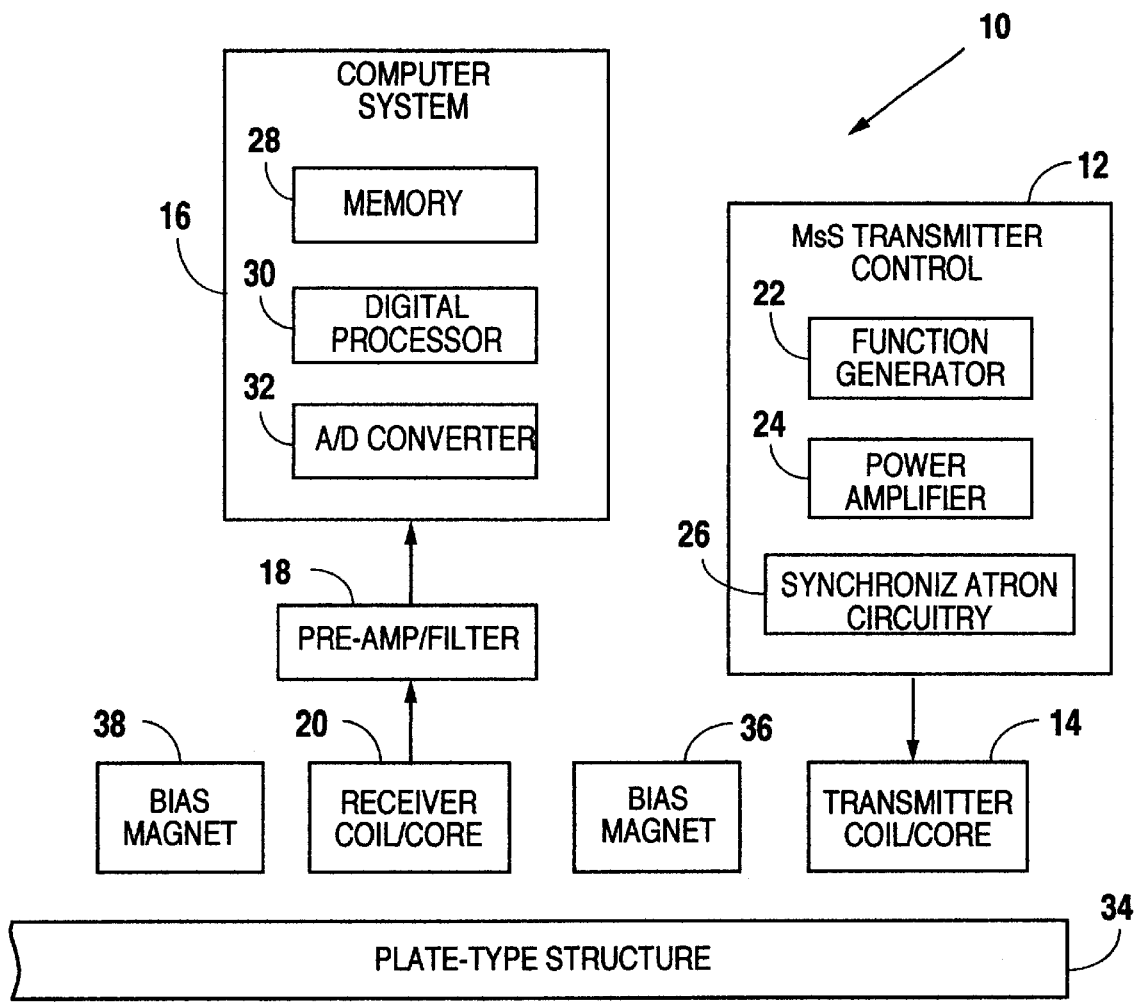
FIG. 1 is a schematic block diagram showing the components of the system of the present invention.

As indicated above, the present invention utilizes the basic methodological approach of earlier developed magnetostrictive sensor techniques associated with the inspection of cylindrical structures such as pipe, tubes, and the like. The basic system of such techniques is combined with a novel magnetostrictive sensor for application to plate type structures. Reference is made first to FIG. 1 for a general description of the complete system utilized to carry on the inspection of a plate type structure. Inspection system 10 includes a magnetostrictive sensor transmitter control 12 and an associated transmitter coil/core 14. Transmitter coil/core 14 is positioned adjacent to the surface of plate type structure 34. Also positioned near the surface of plate type structure 34 is receiver coil/core 20. Receiver coil/core 20 is positioned to detect reflected waves within plate type structure 34 and to thereby generate a signal representative of the wave characteristics that are reflected from a defect present in the structure. Receiver coiVcore 20 is connected to preamp/filter 18 which in turn is connected to computer system 16.

Magnetostrictive sensor transmitter control 12 is comprised of function generator 22, power amplifier 24, and synchronization circuitry 26. These elements together generate an appropriate signal for driving transmitter coil/core 14 and thereby generate guided waves within plate type structure 34.

Computer system 16 is comprised of memory 28, digital processor 30, and analog to digital converter 32. These components together receive, digitize, and analyze the signal received from receiver coil/core 20. The signal contains wave characteristics indicative of the characteristics of the reflected guided waves present in plate type structure 34.

Both transmitter coil/core 14 and receiver coil/core 20 have associated with them bias magnets 36 and 38, respectively. Bias magnets 36 and 38 are positioned adjacent the coils/cores 14 and 20 near plate type structure 34 in order to establish a bias magnetic field to facilitate both the generation of guided waves within structure 34 and the appropriate detection of reflected guided waves.

Figure 2:
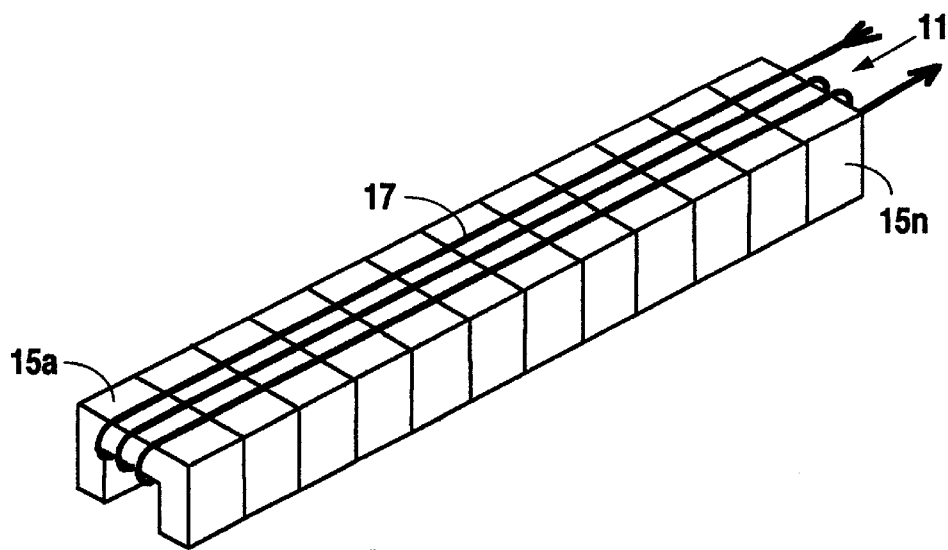
FIG. 2 is a perspective view of a magnetostrictive sensor of the present invention.

Reference is now made to FIG. 2 for a detailed description of the novel magnetostrictive sensor structure utilized in the present invention. Magnetostrictive sensor 11 as shown in FIG. 2 could be utilized as either transmitter coil/core 14 or receiver coil/core 20 described above in FIG. 1. Magnetostrictive sensor 11 is comprised of a plurality of U-shaped cross-sectional cores stacked in a lengthwise direction to form a sensor with a longitudinal axis that is long in comparison to its cross-section. Core elements 15a through 15n in the preferred embodiment may be made from a stack of U-shaped ferrites, transformer steel sheets, mild steel, or permanent magnets. The core elements 18a through 15n could have other shapes; however, U-shaped or E-shaped core elements have been found to be more efficient. If an E-shaped core is used, a transmitter may be located on one part of the E with a receiver on the other part of the E.

Surrounding the stack of U-shaped cores 15a through 15n is wire coil 17. The number of turns for coil 17 is dependent upon the driving current and the magnetic permeability of core 15 and may be varied as is well known in the art.

Figure 3:
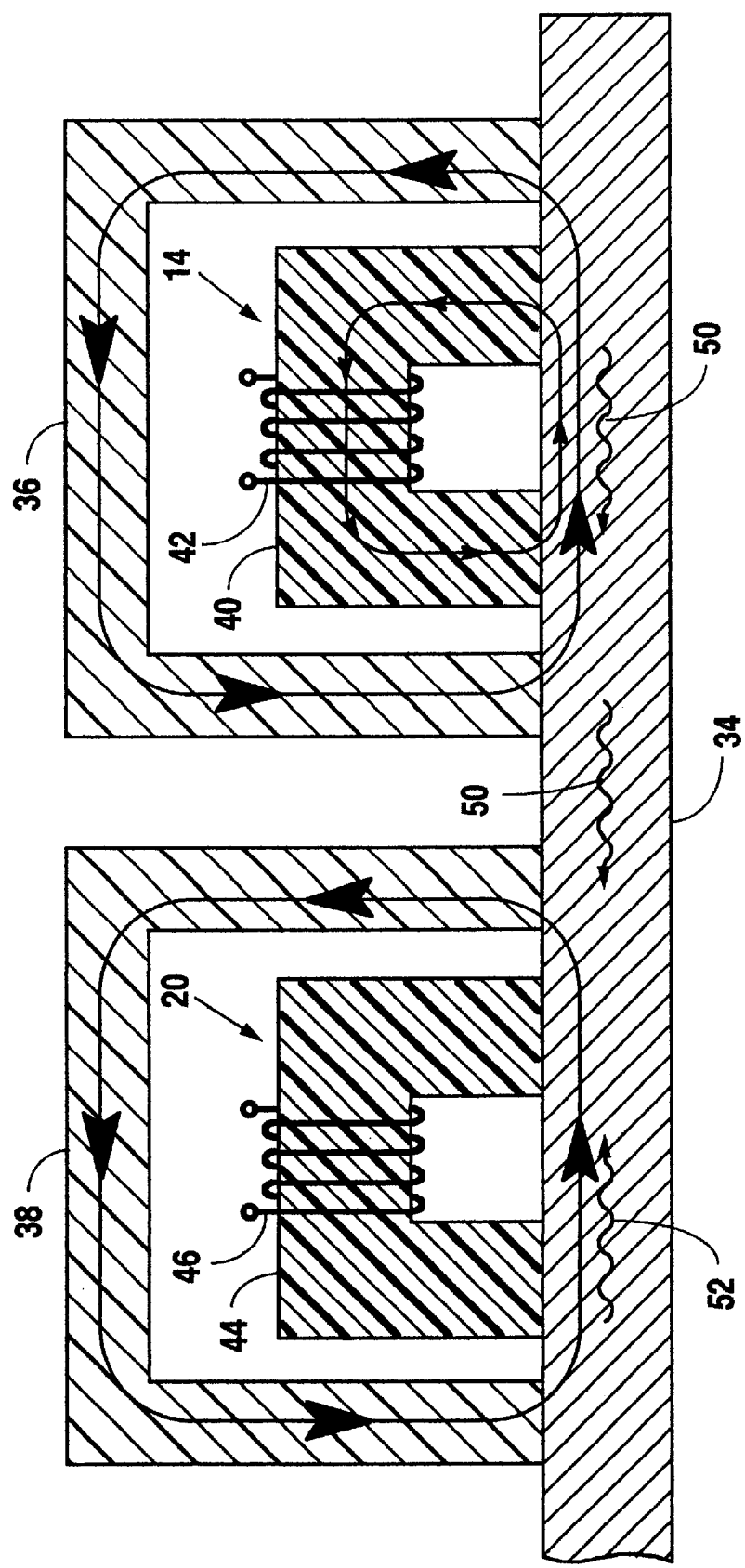
FIG. 3 is a cross-sectional view of the implementation of the sensors of the present invention in conjunction with a plate type structure.

FIG. 3 shows in cross-sectional view the application of a pair of sensors structured as shown in FIG. 2 and implemented in conjunction with the methods of the present invention. In FIG. 3, a cross-section of plate type structure 34 is shown with transmitter coil/core 14 and receiver coivcore 20 positioned on the plate. The view in FIG. 3 of both transmitter coil/core 14 and receiver coil/core 20 is cross-sectional in nature in order to show the establishment of a magnetic flux within plate type structure 34. Associated with each of the coils/cores 14 and 20 are bias magnets 36 and 38. In FIG. 3, bias magnets 36 and 38 are shown placed over coils/cores 14 and 20. It is understood that in the actual implementation of the present invention, bias magnets 36 and 38 may be one or two magnets. What is necessary is that a magnetic field be generated in plate type structure 34 under the transmitter coil/core 14 and the receiver coil/core 20. It is only critical that the DC bias magnetic fields established by bias magnets 36 and 38 are established within the volume of plate type structure 34 under transmitter coil/core 14 and under receiver coil/core 20 as appropriate.

Transmitter coil/core 14 is comprised of core material 40 and coil windings 42. Together these components, as driven by the magnetostrictive sensor transmitter control (not shown), operate to generate changes in the magnetic field established by bias magnet 36 within plate type structure 34. This time-varying or AC magnetic field within plate type structure 34 generates a mechanical, guided wave that propagates in a direction parallel to the surface of plate type structure 34. This guided wave is depicted as wave 50 in FIG. 3 and propagates in a direction away from transmitter coil/core 14. If, as shown in FIG. 3, transmitter coil/core 14 is placed on the surface of plate type structure 34, with the longitudinal axis of coil/core 14 directed into the drawing page in the view shown, wave 50 would propagate in two directions away from the longitudinal axis of coi/lcore 14 and through plate type structure 34. This would serve to investigate the volume of plate type structure 34 bounded by the length (long axis) of the magnetostrictive sensor utilized. In this manner, an inspection "sweep" of a volume of plate type structure 34 can be carried out generally equal in width to the length of the magnetostrictive sensor.

The arrangement of the magnetostrictive sensor utilized as the detection coil in the present invention is essentially the same as the arrangement for the transmitter coil. In FIG. 3, receiver coil/core 20 is comprised of core material 44, shown in cross-section, as well as coil windings 46. Bias magnet 38 is likewise positioned over receiver coil/core 20. This arrangement establishes a bias magnetic field within plate type structure 34 that fluctuates according to the presence of reflected mechanical guided waves within the material adjacent the sensor. In FIG. 3, reflected mechanical waves are depicted as 52 proximate to receiver coil/core 20 and are detected thereby. In this manner, mechanical waves passing through plate type structure 34 under receiver coil/core 20 are detected and "translated" into voltage fluctuations in coil 46 in a manner that generates an appropriate signal for analysis by the balance of the electronics of the system of the present invention (not shown).

As indicated above, the methods and apparatus of the present invention can be utilized in conjunction with discrete magnetostrictive transmitters and receivers or in conjunction with a single magnetostrictive sensor operable as both a transmitter and a receiver. In the latter case, the structures described in FIG. 3 would be limited to a single magnetostrictive sensor of the configuration shown for either transmitter coil/core 14 or receiver coi/lcore 20.

In another alternative approach, one with greater practical application, two transmitter sensors and two receiver sensors may be used when the sensors are controlled by appropriate phasing. In this manner, the direction of the interrogating beam may be controlled. As an example, when the transmitter generates the wave in a first position (+) direction, the return signals may be detected by a receiver controlled to detect waves traveling in the negative (−) direction. As mentioned above, this control is achieved by phasing the two sensors appropriately, a process well known in the field of NDE techniques. In this manner, an inspection of the plate may be carried out first to one side of the transmitting sensor and then by simply switching the sensor instrumentation an inspection may be carried out to the opposite side of the transmitting sensor. Various other inspection techniques known and used with magnetostrictive sensors may likewise apply with the methods and structures of the present invention.

Figure 4:
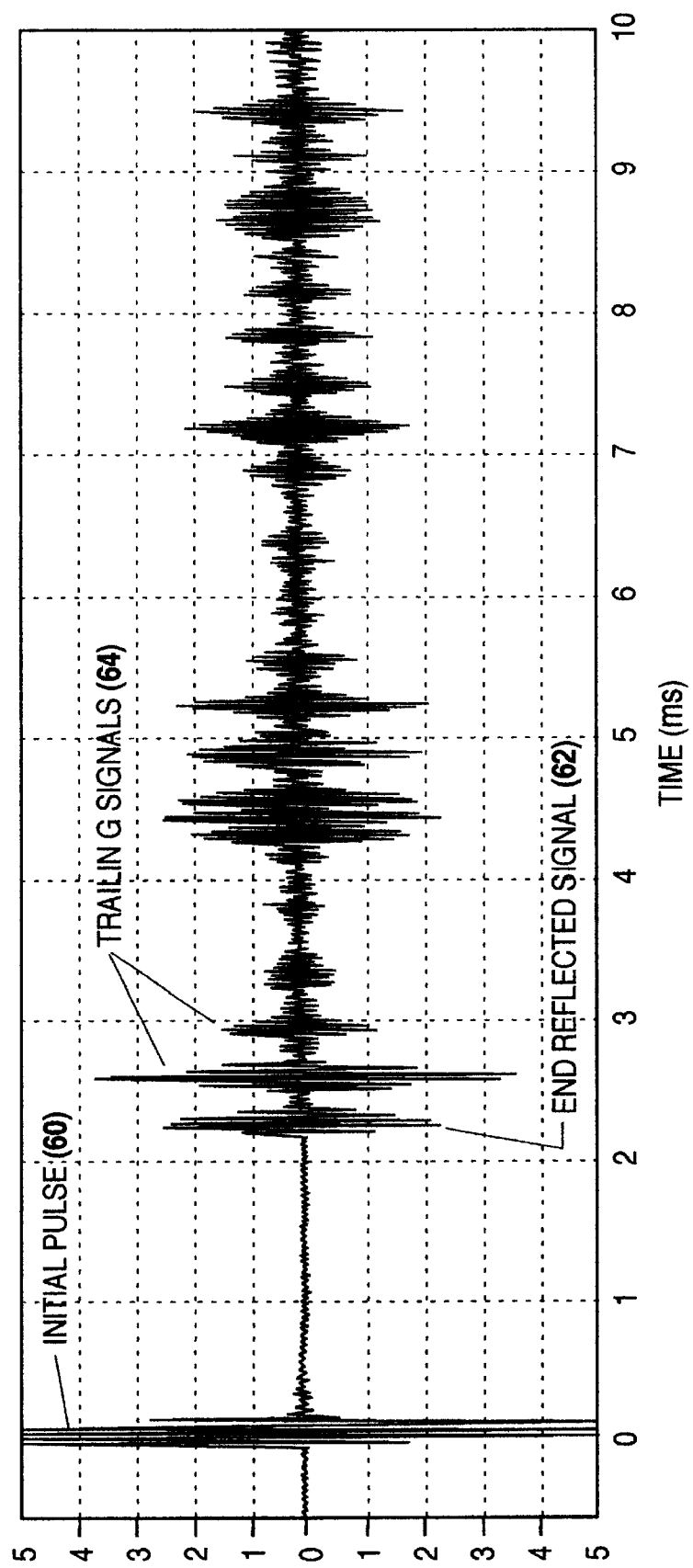
FIG. 4 is a plot of a signal received through the system of the present invention utilizing a 60 kHz $S_0$ wave mode signal in a 4 foot wide, 20 foot long, 0.25 inch thick steel plate.
Figure 5:
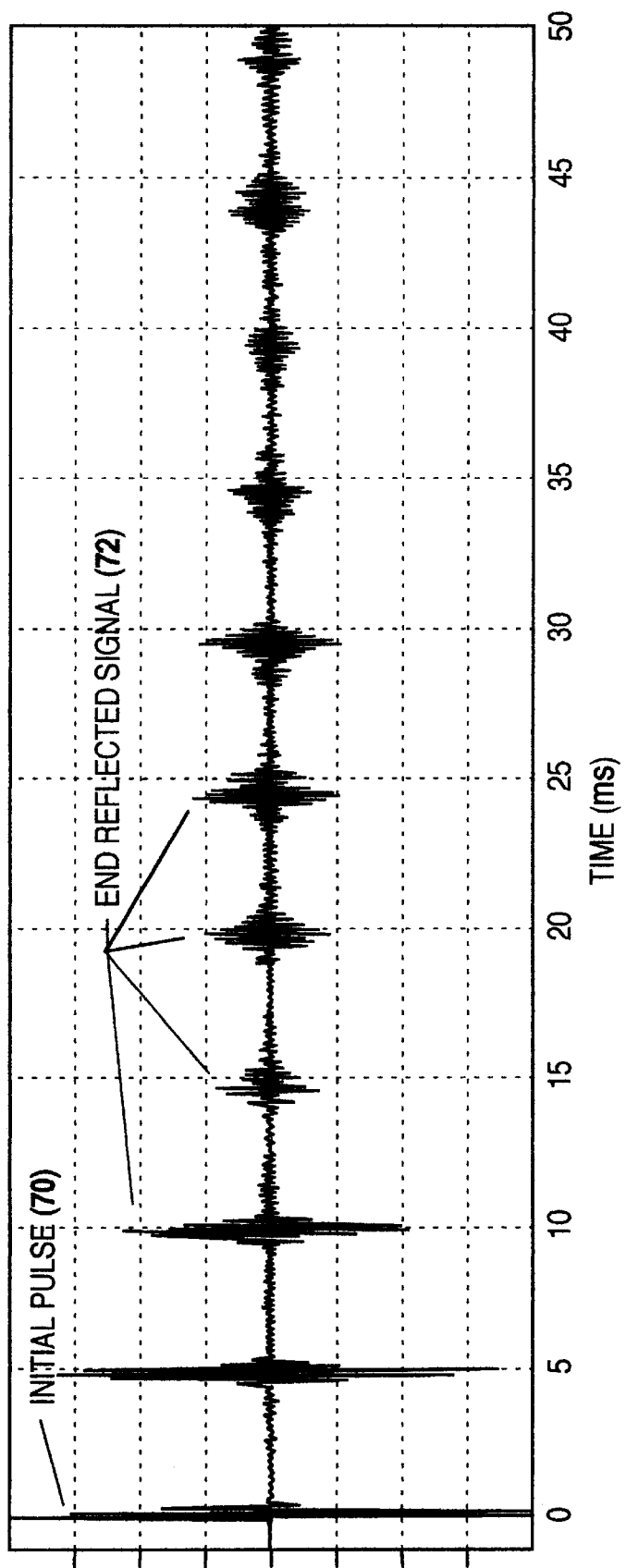
FIG. 5 is a plot of a signal received through the system of the present invention in conjunction with the structure associated with FIG. 4 for a 40 kHz $A_0$ wave mode signal.

Reference is now made to FIGS. 4 and 5 for a detailed description of sample data acquired from a 0.25 inch thick, 20 foot long, and 4 foot wide steel plate investigated by the devices and methods of the present invention.

The signal represented in FIG. 4 shows the first symmetric wave mode ($S_o$) in the plate while the signal depicted in FIG. 5 shows the first anti-symmetric wave mode ($A_o$). FIG. 4 is a time varying amplitude plot of a 60 kHz magnetostrictive sensor signal taken from the above described steel plate geometry. The wave is directed through appropriate orientation of the sensor and propagates in the long direction within the steel plate. The signal components identified in FIG. 4 include the initial pulse 60, end reflected signal 62, and trailing signals 64. Likewise in FIG. 5, initial pulse 70 is indicated, as are end reflected signals 72.

Anomalies within the path of the guided wave generated within the material would, as is known in the art, generate signal components having amplitudes sufficient for identification within either of the two signals shown in FIGS. 4 and 5. In this manner, characteristics of anomalies detected within the plate type structure can be identified and located in the direction of wave propagation away from the magnetostrictive sensor. As is known in the art, the relative location of an anomaly may be identified by the position of the signal characteristic indicative of the anomaly in time relationship with the initial pulse (indicative of the position of the sensor) and the end reflected signals 62 and 72.

Figure 6:
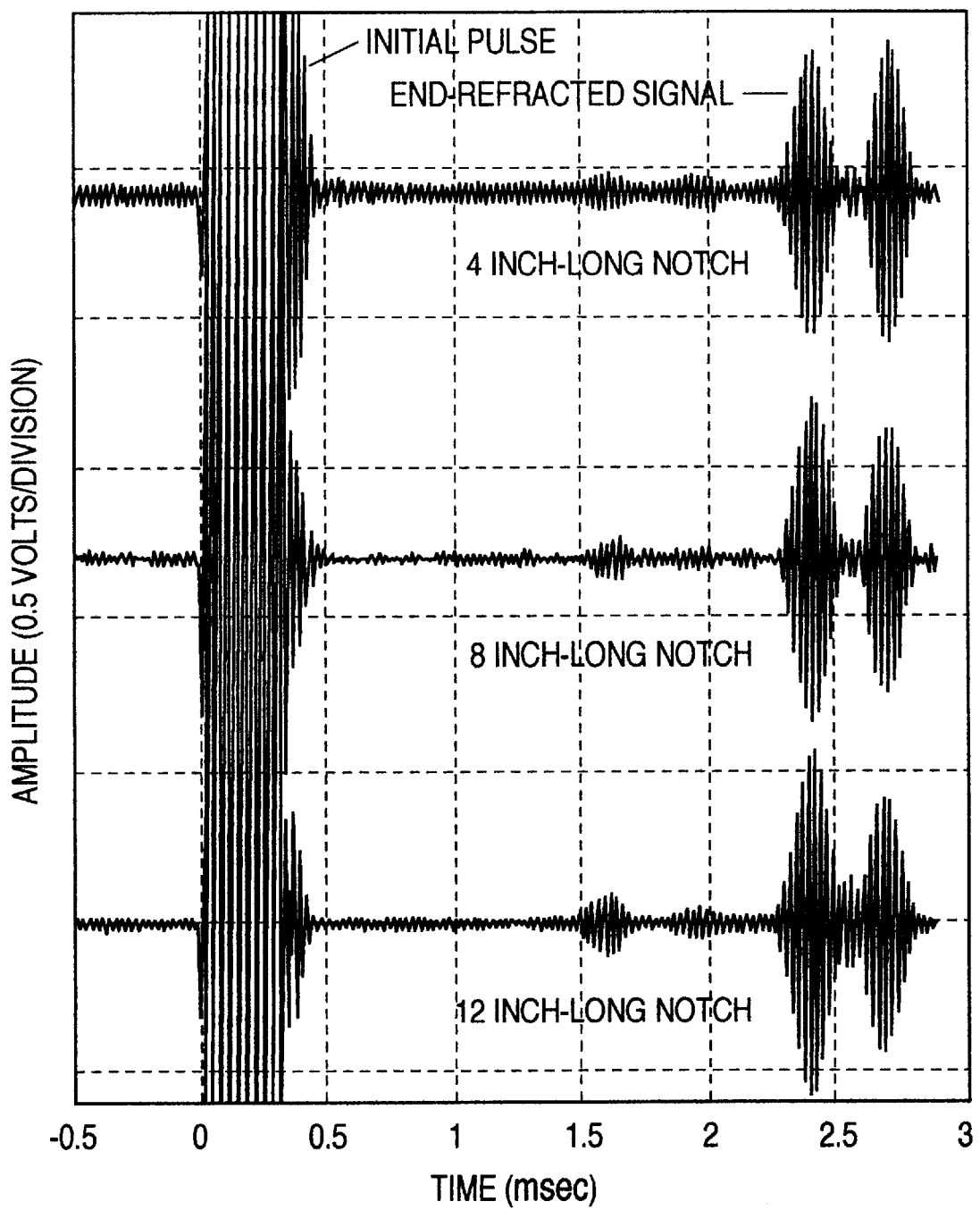
FIG. 6 is a plot of three signals received through the system of the present invention utilizing a 40 kHz $S_0$ wave mode signal in a 4 foot wide, 20 foot long, 0.25 inch thick steel plate.
Figure 7:
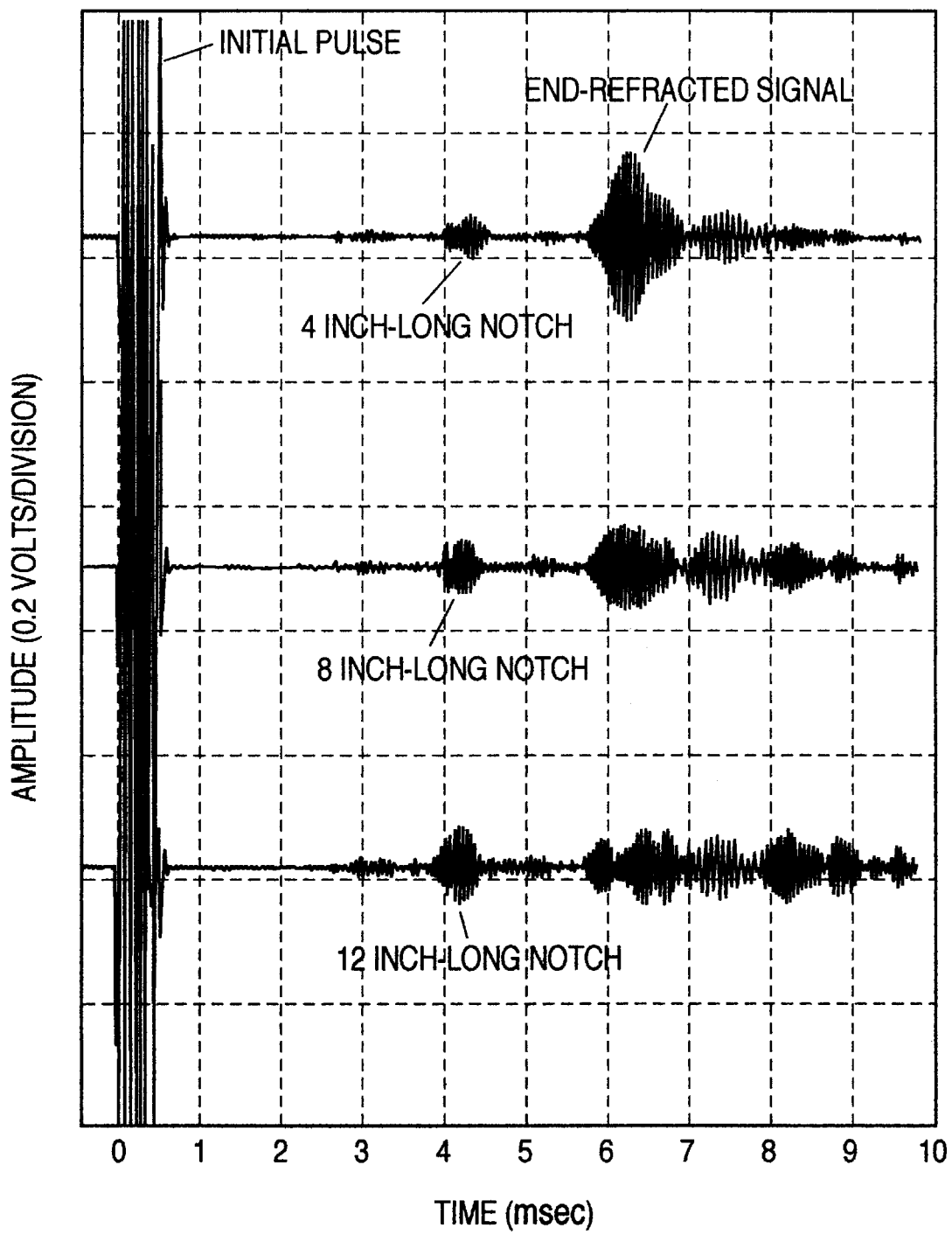
FIG. 7 is a plot of three signals received through the system of the present invention utilizing a 20 kHz $A_0$ wave mode signal in a 4 foot wide, 20 foot long, 0.25 inch thick steel plate.

Examples of such signals are shown in FIGS. 6 and 7. FIG. 6 shows pulse-echo magnetostrictive sensor data for a 40 kHz $S_0$ wave mode signal obtained in a 4 foot wide, 20 foot long, 0.25 inch thick steel plate. Three signals are shown for data collected with a 4 inch long, 8 inch long, and 12 inch long notch cut in the plate at a point approximately two-thirds of the length of the plate away from the sensor.

FIG. 7 shows pulse-echo magnetostrictive sensor data for a 20 kHz $A_0$ wave mode signal obtained in a 4 foot wide, 20 foot long, 0.25 inch thick steel plate. Three signals are also shown for data collected with a 4 inch long, 8 inch long, and 12 inch long notch cut in the plate at a point approximately two-thirds of the length of the plate away from the sensor.

In each case, the notch is not only detectable but may be characterized as to size and position. Various signal analysis techniques may be applied to these signals to discern and characterize other types of anomalies found in such plate-type structures. Discrete fractures and the like are typically identified by isolated reflected waves, while broad deteriorations or corrosions in the plate might be identified by grouped waves received over a period of time. In addition, it is anticipated that signature signals of a particular plate type structure might be acquired prior to implementation of the structure into service. In this manner subsequent signatures may be acquired periodically and compared with the initial base line reference signature to determine the presence of developing anomalies within the plate.

To prove the invention works, symmetric ($S_0$ and antisymmetric ($A_0$) longitudinal wave mode signals were generated and detected using a 12 inch long magnetostrictive probe such as shown in FIG. 2. To generate and detect these wave modes, the bias magnets 36 and 38 are applied in the direction parallel to the direction of wave propagation (perpendicular to the lengthwise length of the magnetostrictive probe). The same probe as shown in FIG. 2 can be used to generate and detect shear horizontal waves in a plate by applying DC bias magnetic fields in a direction perpendicular to the wave of propagation (or parallel to the lengthwise direction of the magnetostrictive probe).

Figure 8B:
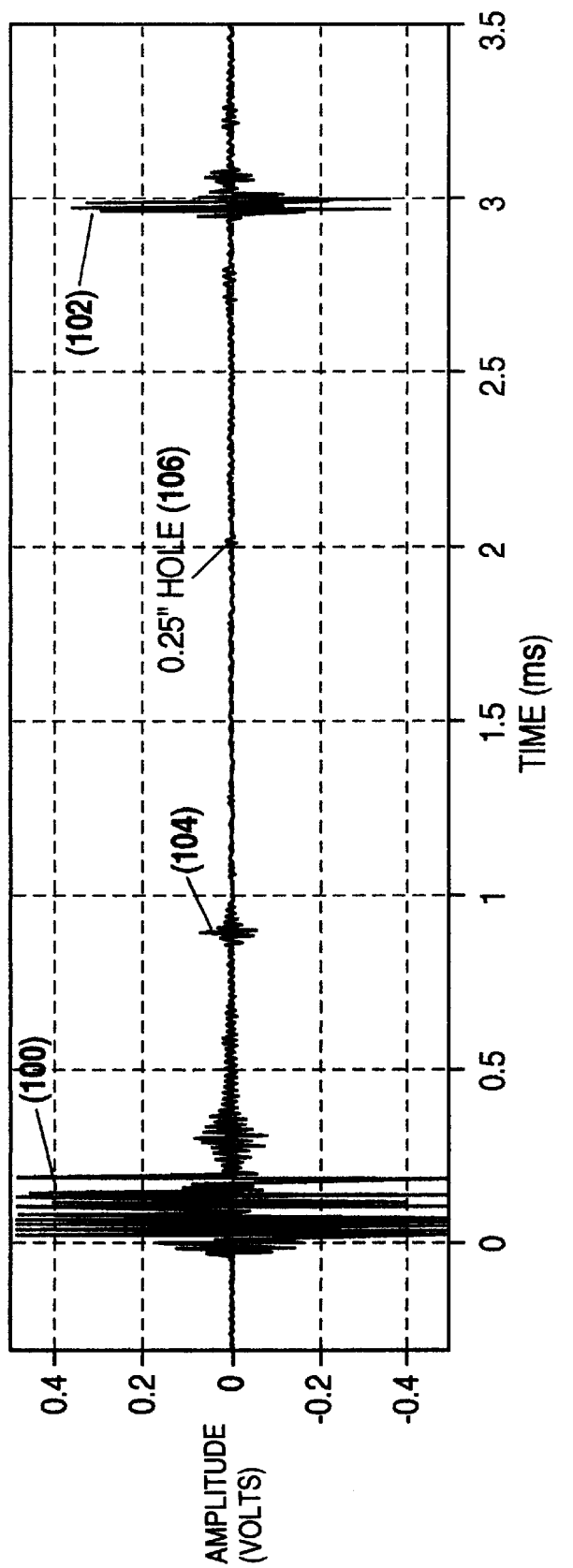
FIGS. 8(a) and (b) are a plot of a shear horizontal wave received through the system of the present invention utilizing an 80 kHz shear horizontal wave in a 4 foot wide, 20 foot long 0.25 inch thick steel plate, before and after a 0.05 inch hole is cut therein.

Using a 4 inch long magnetostrictive probe, a signal was induced in a 0.25 inch thick, 4 foot wide, 20 feet long, steel plate. FIG. 8(a) shows the signal as generated and reflected over time. The initial pulse 100 is generated by the magnetostrictive transmitter controller 12 until it reaches the far end of the sheet and a signal from the far end 102 is received by the receiver coil/core 20. A signal from the near end 104 is received due to the imperfect directionality control of the system.

After drilling a .25 inch hole about two-thirds of the way down the sheet, another initial pulse 100 is sent down the sheet. Again, a signal is received from the near end 104 due to imperfect directionality control. Also, a signal 102 from the far end is received. However, now a signal 106 is received that indicates the 0.25 inch hole in the sheet. Therefore, FIGS. 8(a) and (b) in combination clearly illustrate that shear horizontal waves can be used in the magnetostrictive inspection techniques and probes of the current invention. Also, the magnetostrictive testing of the large plate structures is suitable for low frequency operation (200 kHz or less), has good sensitivity and long range inspection, and is relatively tolerate to liftoff. This is not the case if the inspection technique had used other common nondestructive evaluation techniques, such as electromagnetic acoustic transducers.

Figure 9:
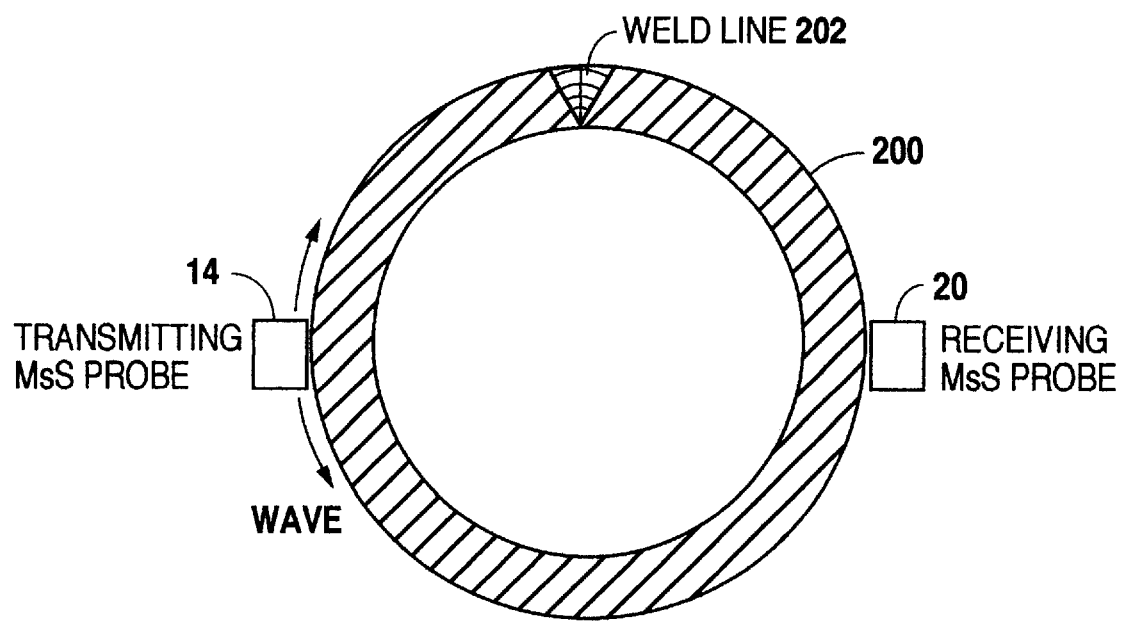
FIG. 9 is a pictorial end view of a welded pipe being inspected using a magnetostrictive transmitting probe and a magnetostrictive receiving probe on opposite sides of the pipe.
Figure 10A:
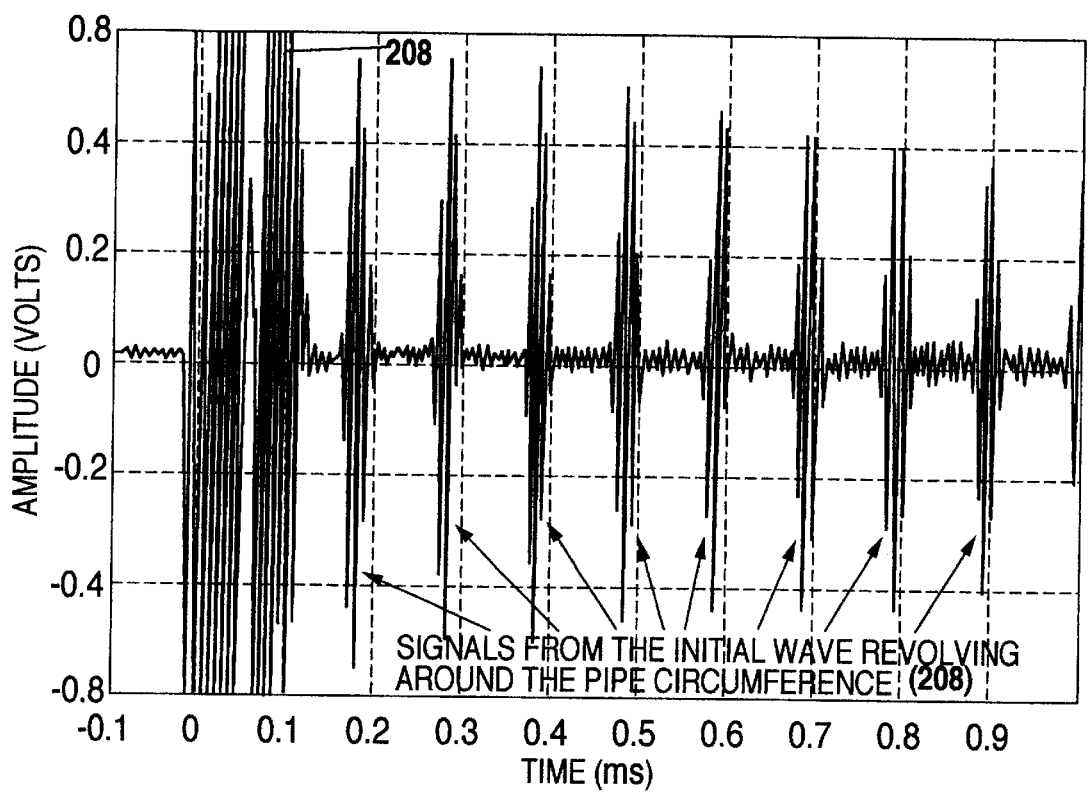
FIGS. 10(a) and (b) are plots of signals received through the system of the present invention when used to test the large diameter pipe as shown in FIG. 9, utilizing a 150 kHz shear horizontal wave mode in a 4.5 inch outside diameter steel pipe having a 0.337 inch thick wall before and after cutting a notch therein.

Pipes can be considered as plates that are simply bent in a circle. Pipes are literally made from sheet metal that is bent into a circle and welded on one side thereof utilizing electric resistance welding. Magnetostrictive inspection techniques may be used to inspect such pipes as shown and explained in connection with FIG. 9, including the electric resistance welding. A pipe 200 is shown with a weld line 202. A transmitter coil/core 14 is located on one side of the pipe 200 and a receiver coil/core 20 is located 180° on the opposite side of the large diameter pipe 200. While not shown, magnetic bias is provided adjacent to the transmitter coiV-core 14 and the receiver coil/core 20. Using the inspection system 10 as shown in FIG. 1, an initial pulse 206 is started around the pipe as shown in FIG. 10(a). Each time the pulse passes the receiver coil/core 20, a signal 208 is received. The signal 208 dies out over a period of time and after repeated revolutions around the pipe 200.

If the transmitter coil/core 14 is 180° around the pipe 200 from the receiver coil/core 20, the two opposite going waves add constructively producing a single large amplitude signal. Once generated, the initial pulse 206 keeps revolving around the circumference of the pipe 200 until all of its energy is dissipated. Therefore, the generated wave produces signals at regular intervals which are equal to the transient time of the shear horizontal wave to travel around the fuill circumference of the pipe 200. If there are any defects at the weld line 202, they will clearly be indicated as defect signals. If the weld line is approximately 90° from transmitter coil/core 14, then the defect would be approximately midway between the signals 208 as received by the receiver coil/core 20.

To prove the measuring of the defects, the applicant, after measuring the signal as shown in FIG. 10(a), cut a notch in the pipe 200. The test was then repeated with an initial pulse 206 inducing a shear horizontal wave around the circumference of the pipe 200. Again, signals 208 indicate each time the shear horizontal wave reaches the receiver coil/core 20. However, in addition, there are notch signals 210 that are created by a reflected signal from the notch that has been induced in the pipe 200. The notch signal 210 increases in amplitude with time because each time the initial wave revolves around the pipe 200, it passes the notch defect thereby producing a notch defect signal 210 which is then added to the previous notch defect signal 210. The increasing of the notch signal 210 occurs for a period of time and then it will decrease until its energy is dissipated, the same as signal 208.

Figure 10B:
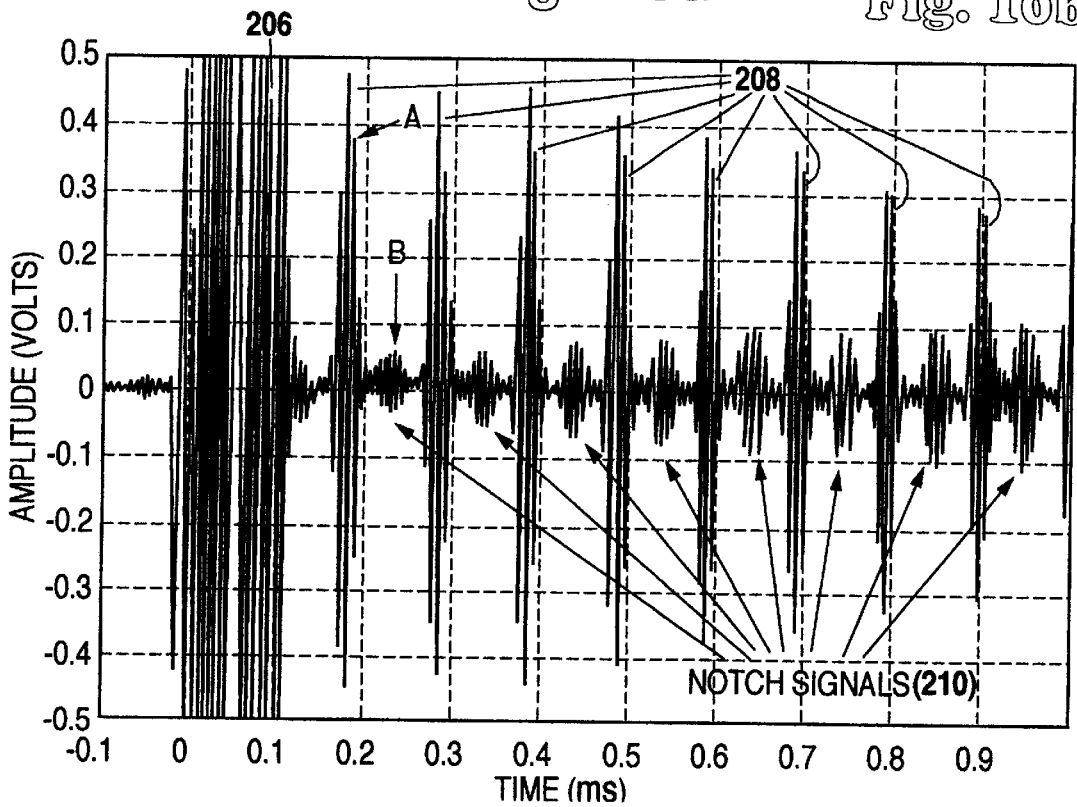

It is possible to get a comparative indication as to the size of the defect by the ratio between the first initial wave signal amplitude 208 and the first defect signal amplitude 210. In the example illustrated in FIG. 10(b), the notch is approximately 8% of the cross-sectional area.

This compares well to the ratio of signal 208 to 210 being approximately 10%. This is intended to be a rough generalization as to the size of the notch. Obviously, other factors would be considered, such as whether the notch is perpendicular or parallel to the direction of travel of the shear horizontal wave.

By use of the method as just described, the present invention can be used to inspect pipes for longitudinal defects and corrosion defects. In the present method, the magnetostrictive probes are moved along the length of pipe to determine any defects in the pipe. In manufacturing facilities, the magnetostrictive transmitters or receivers may be stationary with the pipes moving therebetween and simultaneously being inspected for any defects.

While one of the advantages of the present invention is the ability to carry out broad inspections of large volumes of a plate type structure from a single positioning of the sensor, it is anticipated that the complete investigation of a containment vessel or the like would require multiple placements of the sensor in a variety of positions and orientations. For example, a containment vessel might require the placement of the sensor in a sequential plurality of positions along a predetermined scan line (which could be either horizontal or vertical to the floor) that best achieves the inspection of the entire structure. In this manner, a progressive inspection of an entire containment vessel is carried out without the requirement that all surfaces of the vessel be accessed.

Although a description of a preferred embodiment of the apparatus and method of the present invention has been described, it is anticipated that variations in the manner in which the basic sensor structure of the present invention may be utilized are possible. No specific dimensions for the sensor structure described have been identified as such would be dependent upon the specific plate type structures to be investigated. It is anticipated that sensors of a variety of lengths could be utilized depending upon the requirements of the environment of investigation. In general, the basic structure of the sensor described in the present invention may be utilized wherever ferrogmagnetic plate material is utilized. In such instances where encircling coil type magnetostrictive sensors would not be appropriate, the sensor structure of the present invention provides a mechanism whereby the sensitivity and accuracy of the magnetostrictive investigation technique can be carried out. It is anticipated that other applications of the basic sensor structure described herein will be discerned by those skilled in the art of nondestructive evaluation of materials.

What is claimed is:

1. A method for nondestructive inspection of a plate type ferromagnetic structure, whether flat or curved, for anomalies therein, which anomalies can indicate defects such as notches, cuts, cracks, wear or corrosion, using magnetostrictive techniques, said method comprising the following steps:

first locating a transmitter adjacent to said plate type ferromagnetic structure;

providing a first DC bias magnetic field in said plate type ferromagnetic structure near said transmitter;

second locating a receiver adjacent to said plate type ferromagnetic structure;

providing a second DC bias magnetic field in said plate type ferromagnetic structure near said receiver;

generating a pulse signal in a transmitter control circuit and delivering said pulse signal to said transmitter, said pulse signal causing a fluctuation in said first DC bias magnetic field sufficient to generate guided waves through said plate type ferromagnetic structure as a result of the magnetostrictive effect;

detecting fluctuations in said second DC bias magnetic field as a result of the passage of said guided waves and reflected waves through said plate type ferromagnetic structure, said fluctuations in said second DC bias magnetic field caused by an inversed magnetostrictive effect resulting from said passage of said guided waves or said reflected waves from anomalies within said plate type ferromagnetic structure; and determining if said reflected waves were due to anomalies that should not exist in said plate type ferromagnetic structure;

said transmitter and said receiver having a core with an elongated axis and a coil wound lengthwise therearound so that said guided wave front is parallel to said elongated axis and moves perpendicular thereto.

2. The method for nondestructive inspection of a plate type ferromagnetic structure using magnetostrictive techniques of claim 1 wherein said transmitter and said receiver are a single item and said first DC bias magnetic field and said second DC bias magnetic field are the same.

3. The method for nondestructive inspection of a plate type ferromagnetic structure using magnetostrictive techniques of claim 1 wherein said elongated axis of said transmitter and said receiver are generally parallel to each other.

4. The method for nondestructive inspection of a plate type ferromagnetic structure using magnetostrictive techniques of claim 3 wherein said elongated axis is at least multiples of a width of said core.

5. The method for nondestructive inspection of a plate type ferromagnetic structure using magnetostrictive technique of claim 4 wherein said guided wave front is selected from the group consisting of symmetric, anti-symmetric or shear horizontal waves.

6. The method for nondestructive inspection of a plate type ferromagnetic structure using magnetostrictive techniques of claim 4 wherein said core is made from a stack of U-shaped cores, length of said elongated axis being determined by how many of said U-shaped cores are in said stack.

7. The method for nondestructive inspection of a plate type ferromagnetic structure using magnetostrictive techniques of claim 1 wherein said pulse is less than 200,000 cycles per second.

8. The method for nondestructive inspection of a plate type ferromagnetic structure using magnetostrictive techniques of claim 1 that has good sensitivity, a long inspection range and is relatively tolerant to liftoff by said transmitter or said receiver.

9. A sensor for use in nondestructive testing of plate type ferromagnetic material using magnetostrictive techniques from a pulse signal, said sensor comprising:

an elongated core, length of said core being much longer than its width;

a coil wound around said length of said elongated core;

DC bias magnetic field created in said plate type ferromagnetic material along said elongated core;

a magnetostrictive sensor transmitter control for generating said pulse signal for driving said sensor; and said sensor formed thereby being adapted to receive said pulse signal to generate a magnetostrictive wave front in said plate type ferromagnetic material parallel to the length of said elongated core but in a direction perpendicular thereto and to detect reflected magnetostrictive waves from anomalies therein.

10. The sensor for use in nondestructive testing of plate type ferromagnetic material of claim 9 wherein said elongated core is U-shaped.

11. The sensor for use in nondestructive testing of plate type ferromagnetic material using magnetostrictive techniques of claim 9 wherein the number of turns of said coil determines the strength of said magnetostrictive wave front.

12. The sensor for use in nondestructive testing of plate type ferromagnetic material using magnetostrictive techniques of claim 10 wherein said core is made of a stack of U-shaped cores, said length being determined by how many U-shaped cores are in said stack.

13. The sensor for use in nondestructive testing of plate type ferromagnetic material using magnetostrictive techniques of claim 11 wherein said pulse signal and said reflected magnetostrictive waves are less than 200,000 cycles per second.

14. The sensor for use in nondestructive testing of plate type ferromagnetic material using magnetostrictive techniques of claim 13 wherein said DC bias magnetic field is provided by said core.

15. The sensor for use in nondestructive testing of plate type ferromagnetic material using magnetostrictive techniques of claim 13 wherein said elongated, U-shaped core is selected from the group consisting of U-shaped ferrites, transformer steel sheets, mill steel or permanent magnets.

16. The sensor for use in nondestructive testing of plate type ferromagnetic material using magnetostrictive techniques of claim 13 wherein said sensor has good sensitivity, long inspection range and is relatively tolerant to liftoff.

17. The sensor for use in nondestructive testing of plate type ferromagnetic material using magnetostrictive techniques of claim 9 wherein a first DC bias magnetic field, elongated, U-shaped core and coil generates said magnetostrictive wave front and a second DC bias magnetic field, elongated, U-shaped core and coil detects said reflected magnetostrictive waves.

* * * * *